United States Patent
Viola et al.

(10) Patent No.: US 7,967,181 B2
(45) Date of Patent: Jun. 28, 2011

(54) ROTARY KNIFE CUTTING SYSTEMS

(75) Inventors: Frank J. Viola, Sandy Hook, CT (US); Eric J. Taylor, Middletown, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 222 days.

(21) Appl. No.: 12/184,298

(22) Filed: Aug. 1, 2008

(65) Prior Publication Data
US 2009/0056515 A1 Mar. 5, 2009

Related U.S. Application Data

(60) Provisional application No. 60/966,621, filed on Aug. 29, 2007.

(51) Int. Cl.
*A61B 17/04* (2006.01)
(52) U.S. Cl. .................. 227/180.1; 227/175.1; 606/219
(58) Field of Classification Search .... 227/175.1–182.1; 606/215, 219
See application file for complete search history.

(56) References Cited

U.S. PATENT DOCUMENTS

| | | | | |
|---|---|---|---|---|
| 4,257,299 | A | * | 3/1981 | Aykut ............................. 83/482 |
| 5,222,963 | A | * | 6/1993 | Brinkerhoff et al. ......... 606/153 |
| 5,758,814 | A | * | 6/1998 | Gallagher et al. ......... 623/23.72 |
| 5,797,941 | A | * | 8/1998 | Schulze et al. ............... 606/171 |
| 7,559,453 | B2 | * | 7/2009 | Heinrich et al. ........... 227/180.1 |
| 2004/0000605 | A1 | * | 1/2004 | McPherson et al. ............ 241/30 |
| 2008/0077123 | A1 | * | 3/2008 | Boyden et al. .................. 606/13 |
| 2009/0112243 | A1 | * | 4/2009 | Boyden et al. ................ 606/167 |
| 2009/0177202 | A1 | * | 7/2009 | May et al. ....................... 606/79 |
| 2010/0121141 | A1 | * | 5/2010 | Rontal .......................... 600/106 |

FOREIGN PATENT DOCUMENTS

| EP | 0503689 | 9/1992 |
|---|---|---|
| WO | WO02/071954 A | 9/2002 |

OTHER PUBLICATIONS

European Search Report for corresponding EP 08252805 date of mailing is Nov. 17, 2008 (3 pages).

* cited by examiner

*Primary Examiner* — Paul R Durand

(57) ABSTRACT

There are disclosed rotary cutting systems for use with circular surgical stapling devices. The rotary cutting systems generally include a circular knife blade and a mainspring for imparting rotary motion to the circular knife blade. A latch mechanism is provided to maintain the knife blade on a linear travel path during a first predetermined distance and to release the circular knife blade for rotation due to the bias of the mainspring along a second predetermine distance. The circular knife blade may be rotated by the mainspring itself or, in an alternative embodiment, may be driven by frictional engagement with a rotational hammer.

10 Claims, 11 Drawing Sheets

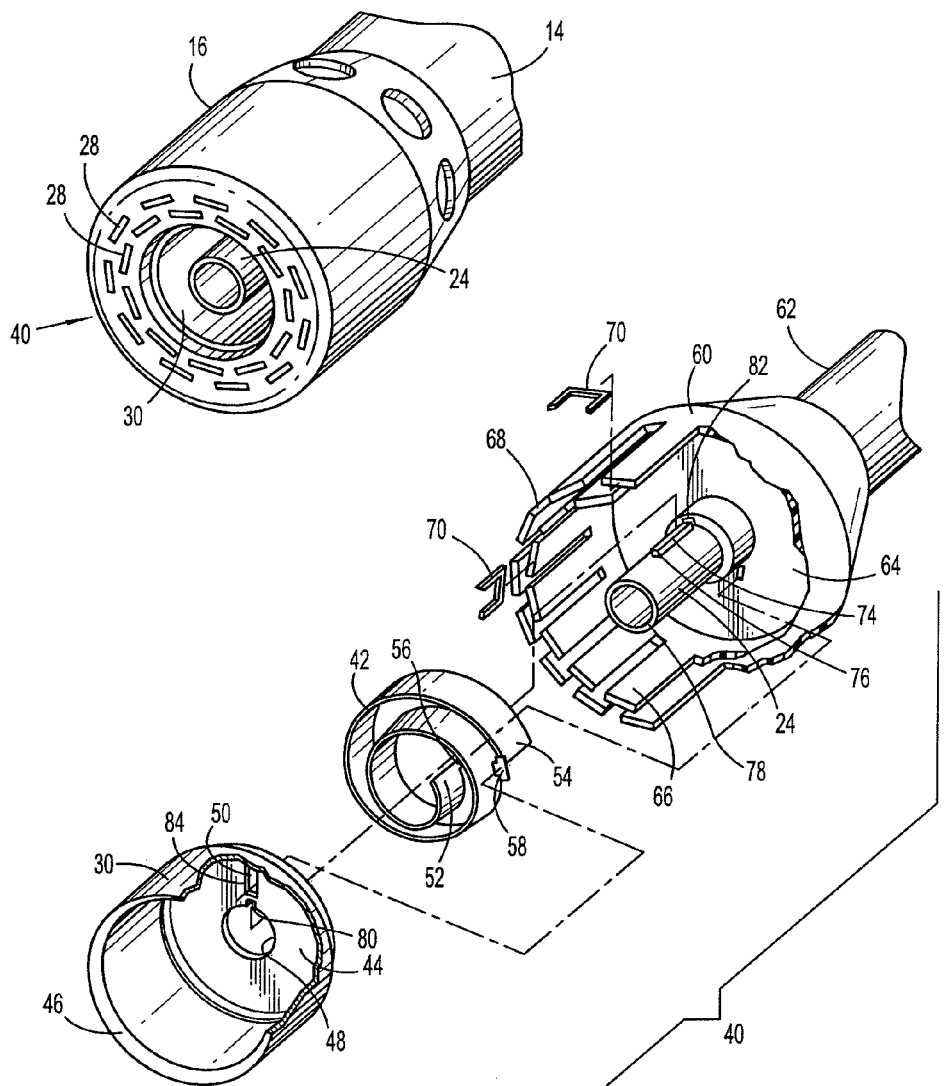

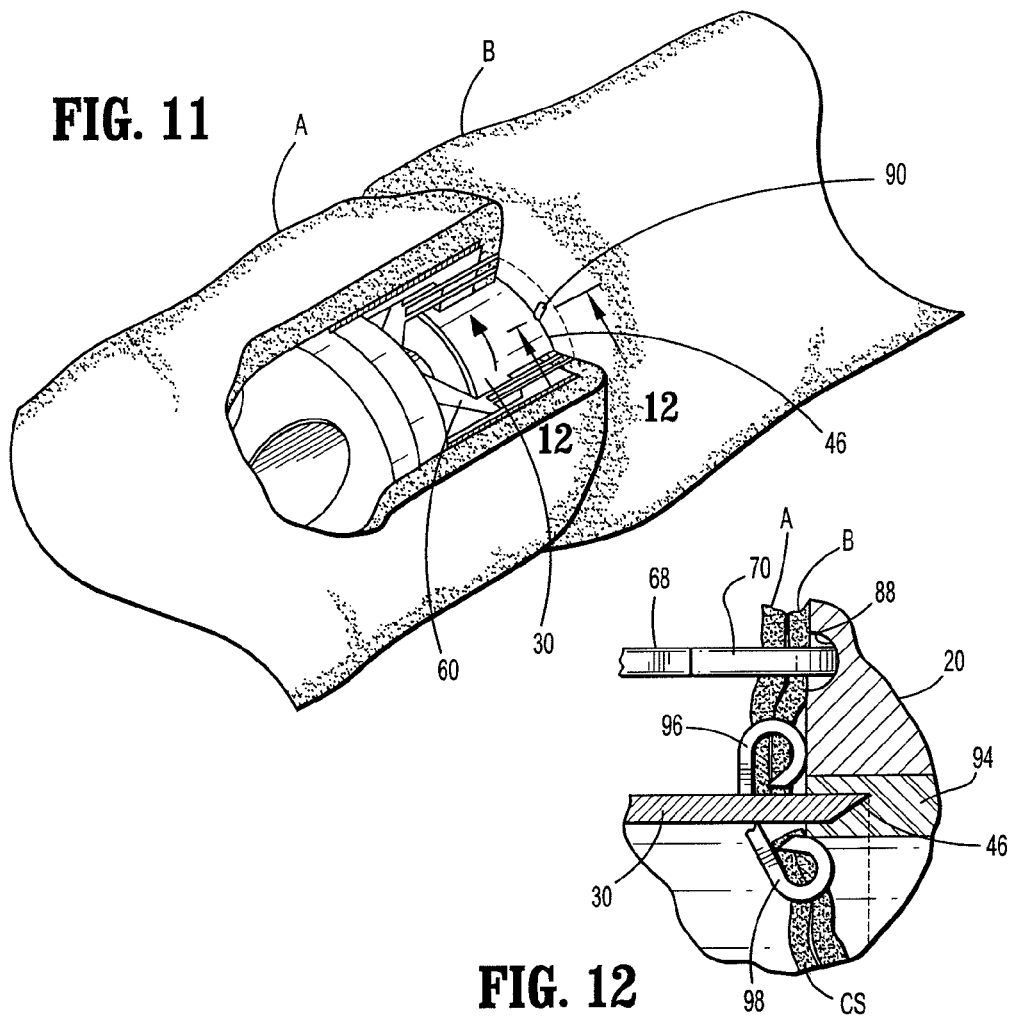
FIG. 11
FIG. 12
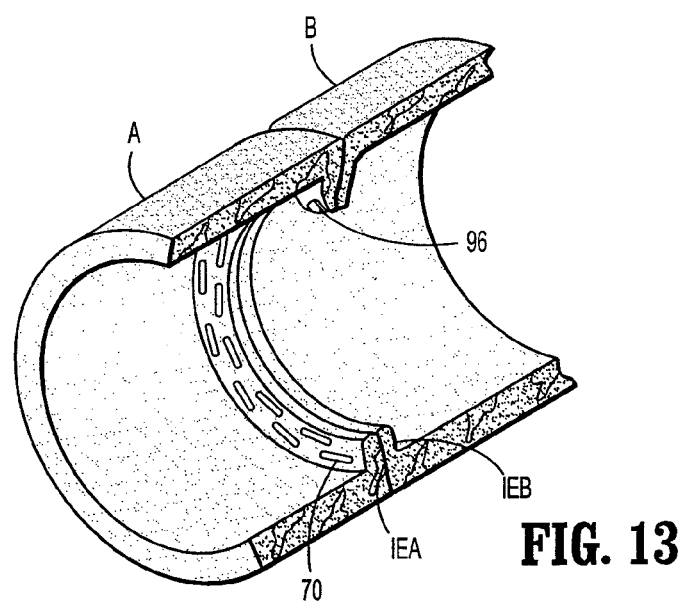
FIG. 13

ROTARY KNIFE CUTTING SYSTEMS

CROSS REFERENCE TO RELATED APPLICATION

The present application claims the benefit of and priority to U.S. Provisional Application Ser. No. 60/966,621 filed on Aug. 29, 2007, the entire contents of which are incorporated herein by reference.

BACKGROUND

1. Technical Field

The present disclosure relates to rotary knife cutting systems. More particularly, the present disclosure relates to rotary knife cutting systems for use with surgical stapling devices.

2. Background of Related Art

During various surgical procedures, it is often necessary to cut out or excise a diseased section of tubular tissue. This is typically accomplished by using a linear stapling device which cuts across the long axis of the tubular tissue leaving a transverse row of staples extending across the edge of the cut tissue. In appearance, the cut and stapled edge of the tubular tissue resembles a duckbill in form. This procedure is performed on both sides of the diseased tissue section leaving two stapled free duckbilled edges of tissue to be joined. This is typically termed "forming an anastomosis", i.e., reconnecting two free ends of hollow tubular tissue sections.

In order to reconnect to tissue sections, a circular stapling device is inserted in a first tubular tissue section and an anvil member of the circular stapling device is inserted in the opposite tubular tissue section. The duckbilled edges of the tubular tissue sections are cinched down against shafts associated with the anvil member and the staple head. The anvil member is then moved adjacent a staple head of the circular stapling device and the circular stapling device is actuated to drive a circular array of staples from the staple head through the tubular tissue sections and into the anvil member. During the procedure, a circular knife blade is advance through the tissues to cut or core out the duckbilled staple sections of the two tubular tissue sections. Upon removal of the surgical stapling device, an anastomosis is formed by the circular array of staples joining the two tubular tissue sections.

In some instances, when the duckbilled sections of the tubular tissue sections are cinched down against the shafts of the circular stapling device, some of the staples resulting from the use of the linear surgical stapling device may be left in the path of the advancing blade of the circular stapling device. Thus, the circular knife blade associated with the circular stapling device needs to cut through these displaced or "wayward" staples. A need exists for rotary cutting system for use in a circular surgical stapling device capable of rotating a knife blade so as to slice through wayward staples and any tough tissue to thereby insure a proper anastomosis between two tubular tissue sections. There is also a need for a latch mechanism for use with a rotary cutting system to prevent premature rotation of a knife blade until such time as the tubular tissue sections have been stapled with a circular array of staples.

SUMMARY

There is disclosed a rotary cutting system for use with a surgical stapling device. The rotary cutting system generally includes a knife blade having a distal cutting edge and a proximal base, a support base positioned within the surgical stapling device and a mainspring for imparting motion to the knife blade relative to the support base. The rotary cutting system also includes a releasable latch mechanism engagable with the knife blade to releasably restrain the knife blade against the bias of the mainspring.

The mainspring is a length of material spiral coiled upon itself and expandable from a wound condition storing energy to an expanded condition releasing energy such that the mainspring imparts a rotary motion to the knife blade relative to the support base as the mainspring moves from the wound condition to the expanded condition. A first end of the mainspring is attached to the support base and a second end of the mainspring is engageable with the knife blade. The first end of the mainspring is located radially inward of the second end of the mainspring. In one embodiment, the mainspring is a length of spring steel.

The disclosed knife blade is a circular cutting blade. The second end of the mainspring is engagable with the proximal base of the knife blade. In one embodiment, the distal cutting edge of the knife blade is angled relative to the proximal base of the knife blade. In an alternative embodiment the distal cutting edge of the knife blade is serrated or otherwise configured or treated to enhance cutting.

The proximal base of the knife blade has a slot and the second end of the mainspring has a tab engagable within the slot such that the tab moves radially outward within the slot as the mainspring moves from the wound condition to the expanded condition.

In one embodiment of the rotary cutting system, the support base is a staple pusher positioned within a staple head of the surgical stapling device.

The knife blade, mainspring and staple pusher are movably mounted on a longitudinal shaft inside the staple head such that the knife blade is longitudinally movable along the shaft. The latch mechanism includes a protrusion formed on the shaft and a notch formed in the knife blade. The notch in the knife blade is engageable with the protrusion such that the knife blade is restrained against rotary motion when the notch is engaged with the protrusion and is free to rotate due to the bias of the mainspring when the notch is disengaged from the protrusion.

There is also disclosed a rotary cutting system for use with a surgical stapling device including a knife blade having a distal cutting edge and a proximal base, a support base positioned within a surgical stapling device and a mainspring for imparting motion to the knife blade relative to the support base. In this embodiment, a hammer member is interposed between the knife blade and the mainspring. The hammer member is engagable with the proximal base of the knife blade. A first end of the mainspring is attached to the support base and a second end of the mainspring is engageable with the hammer member.

The hammer member has a first surface engagable with the proximal base of the knife blade. The hammer member fricitionally engages the proximal base of the knife blade to rotate the knife blade.

The mainspring is releasable from a wound condition storing energy to an expanded condition releasing energy such that the mainspring imparts a rotary motion to the hammer member as the mainspring moves from the wound condition to the expanded condition. The hammer member has a slot and the second end of the mainspring has a tab engagable with the slot such that the tab moves radially outward in the slot as the mainspring moves from the wound condition to the expanded condition. The disclosed rotary cutting system further includes a latch mechanism engagable with the hammer member to releasably restrain the hammer member against the bias of the mainspring.

DESCRIPTION OF THE DRAWINGS

Various embodiments of the presently disclosed rotary knife cutting system for use with a surgical stapling device are disclosed herein with reference to the drawings, wherein:

FIG. 2 is an enlarged perspective view of a stapling head of the stapling device of FIG. 1;

FIG. 3 is a perspective view, with parts separated, of the stapling head of FIG. 2;

FIG. 11 is a perspective view, partially shown in section, of the tubular tissue sections during actuation of the surgical stapling device to staple and cut areas of the tubular tissue sections;

FIG. 12 is an enlarged side view taken along line 12-12 of FIG. 11;

FIG. 13 is a perspective view, shown in section, of the stapled and cut tissue sections;

DETAILED DESCRIPTION OF EMBODIMENTS

Embodiments of the presently disclosed rotary knife cutting systems for use in a circular surgical stapling device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
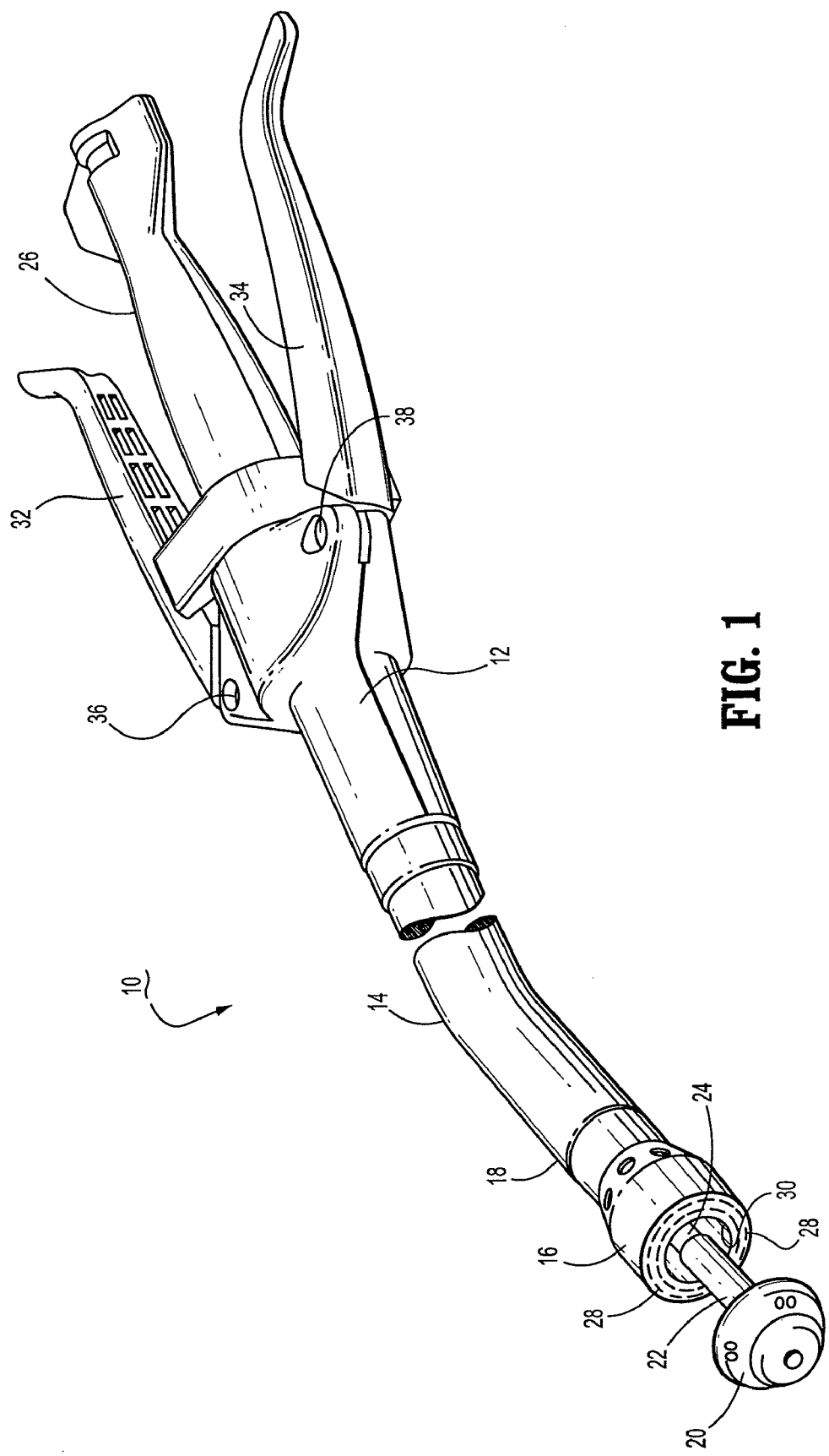
FIG. 1 is a perspective view of a surgical stapling device incorporating one embodiment of a rotary knife cutting system.

Referring to FIG. 1 there is illustrated a surgical stapling device incorporating one embodiment of the presently disclosed rotary cutting system. Stapling device 10 generally includes a body portion 12 and an elongate tubular member 14 extending distally from body portion 12. A staple head 16 is mounted on a distal end 18 of elongate tubular member 14 and contains staples (not shown) for stapling tissue sections together in a manner described in more detail hereinbelow.

Stapling device 10 also includes an anvil member 20 for crimping the staples ejected from staple head 16 after they pass through tissue. An anvil shaft 22 is attached to anvil member 20 and is removably engagable with a shaft 24 located within staple head 16. A tail member 26 is rotatably mounted on body portion 12 and is operable on shaft 24 to move shaft 24 longitudinally within staple head 16. Rotation of tail member 26 moves shaft 24, and thus anvil shaft 22 connected thereto, to move or approximate anvil 20 relative to staple head 16.

Staple head 16 includes a plurality of staple containing pockets 28 for stapling tissue and a knife blade 30 associated with a novel rotary cutting system as described in more detail hereinbelow. A pair of arms, 32 and 34, are pivotally connected to body portion 12 at pivot points 36 and 38, respectively. Arms 32 and 34 are operable to eject staples contained in staple pockets 28 through tissue and into anvil 20 and to advance knife blade 30 to cut or core tissue captured between staple head 16 and anvil member 20.

Referring now to FIGS. 2 and 3, and initially with respect to FIG. 2, there is disclosed a novel rotary cutting system 40 located within staple head 16. Rotary cutting system 40 is provided to impart a rotary motion to knife blade 30. Imparting a rotating motion to knife blade 30 enhances the ability of knife blade 30 to slice through staples or other hard matter, including tough tissues.

Referring now to FIG. 3, rotary cutting system 40 generally includes knife blade 30 and a power source or mainspring 42 to provide a rotating drive force to knife blade 30. Knife blade 30 is a circular cutting blade and has a relatively flat proximal base 44 and a circular distal cutting edge 46. A circular opening 48 is provided in base 44 and fits over shaft 22. This allows knife blade 30 to move longitudinally along shaft 24 as well as to rotate relative to shaft 24. Base 44 also includes a radially extending longitudinal slot 50 which allows a portion of mainspring 42 to move outward as mainspring 42 imparts a rotary motion to knife blade 30 in a manner described in more detail hereinbelow.

Figure 21:
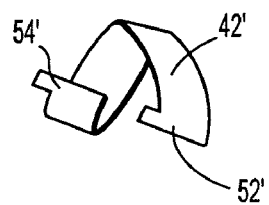
FIG. 21 is a perspective view of an alternate embodiment of the spring.

Mainspring 42 is formed from a length of material coil wound upon itself and having memory characteristics which allows mainspring 42 to move from a first or wound condition storing energy to a second or expanded condition releasing the stored energy. Mainspring 42 can be formed from a variety of materials such as, for example, stainless steel, shape memory alloys, etc. Mainspring 42 has a first end 52 and a second end 54. When mainspring 42 is wound into a coil form, first end 52 of mainspring 42 is located radially inward of second end 54. A first tab 56 is located on first end 52 of mainspring 42 and is configured to engage and anchor first end 52. A second tab 58 is located on second end 54 and is positioned within slot 50 of knife blade 30. Second tab 58 moves within slot 50 as mainspring 42 moves from the wound condition to the expanded condition. In the alternate embodiment of FIG. 21, the ends 52' and 54' of mainspring 42' are axially offset.

Rotary cutting system 40 further includes a pusher 60 which, among other things, serves as an anchor point for first end 52 of mainspring 42. Pusher 60 includes a proximal drive shaft 62 for moving pusher 60 along shaft 24. Pusher 60 includes a base 64 having first and second circular arrays of pusher fingers 66 and 68, respectively, extending distally from base 64. Pusher fingers 66 and 68 are longitudinally movable within staple pockets 28 formed in staple head 16 (FIG. 2) to eject staples, such as, for example generally U-shaped staples 70, out of staple pockets 28 and into tissue. A notch 72 is provided within base 64 of pusher 64 receipt of tab 56 formed on first end 52 of mainspring 42.

In one embodiment, rotary cutting system 40 further includes a latch mechanism for releasably restraining knife blade 30 against rotary motion due to the force of mainspring 42. The disclosed latch mechanism allows knife blade 30 to move longitudinally along shaft 22 for a predetermined distance without rotation and, upon release of the latch mechanism, allows knife blade 30 to rotate due to mainspring 42. The disclosed latch mechanism generally includes a protrusion or longitudinally extending rib 74 formed on shaft 24. A distal end 76 of rib 74 terminates proximally of a distal end 78 of shaft 24. The length of rib 74 along shaft 24 restrains knife blade 30 against rotation for a predetermined distance as knife blade 30 moves longitudinally within staple head 16 to cut or core tissue. Knife blade 30 has a notch 80 formed in circular opening 48 which is configured to engage and ride along rib 74 as knife blade 30 moves longitudinally relative to shaft 24. Once notch 80 has cleared distal end 76 of rib 74, knife blade 30 is free to rotate. Pusher 60 also has a notch 82 allowing pusher 60 to move distally along shaft 24 and rib 74.

In assembling rotary cutting system 40, first tab 56 formed on first end 52 of mainspring 42 is inserted into notch 72 provided in base 64 of pusher 60. Mainspring 42 is wound tightly upon itself in coil fashion and second tab 58 formed on second and 54 of mainspring 42 is inserted within slot 50 formed in base 44 of knife blade 30. Positioning of knife blade 30 along shaft 24 such that longitudinal ribs 74 engages notch 80 restrains mainspring 42 in a wound condition storing energy for later release to impart a rotary motion to knife blade 30.

Figure 4:
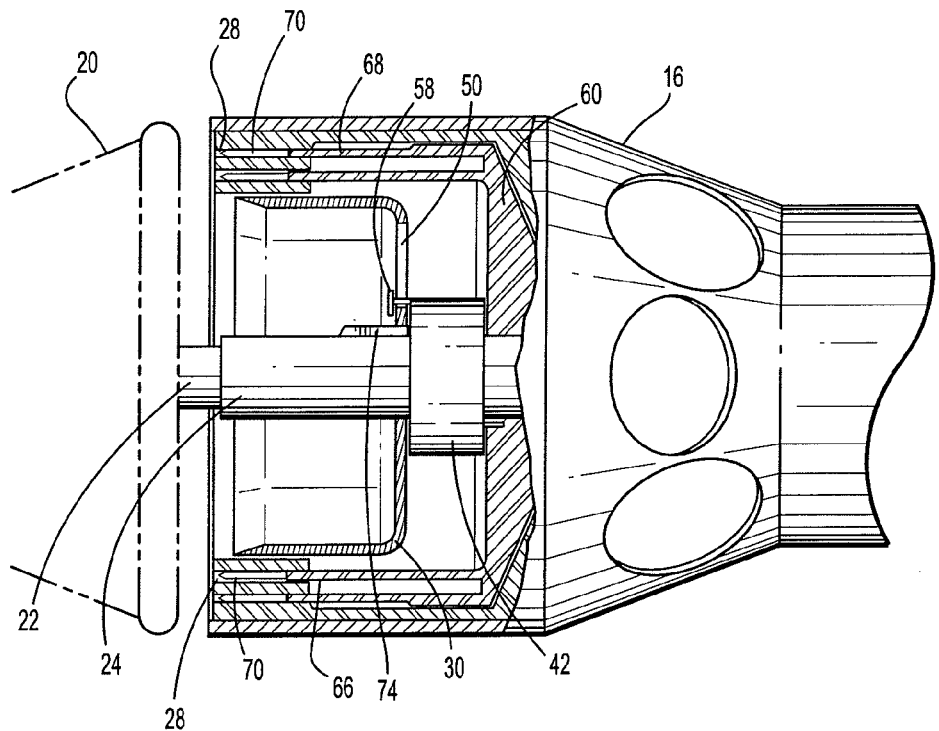
FIG. 4 is a side view, partially shown in section, of the surgical stapling head in an initial, pre-fired condition.

Referring now to FIGS. 4-7, the mechanical operation of rotary cutting system 40 including the disclosed latch mechanism will now be described. Referring initially to FIG. 4, in the initial condition, knife blade 30 and pusher 60 are in a proximal most position within staple head 16. Staples 70 are positioned within staple pockets 28 ahead of first and second arrays of pusher fingers 66 and 68. Mainspring 42 is in a wound condition storing energy with second end 58 located radially inwardly within slot 50 of knife blade 30. Knife blade 30 is restrained against rotary motion by engagement with rib 74 on shaft 24 as described hereinabove. Anvil member 20 is attached to staple head 16 by engagement of shaft 22 with shaft 24.

Figure 5:
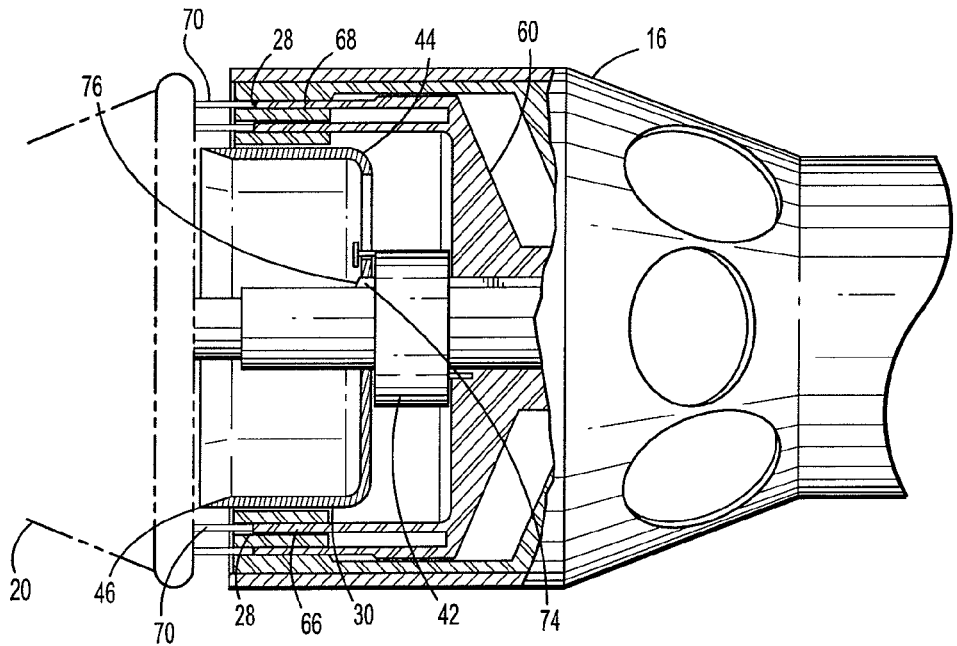
FIG. 5 is a side view, partially shown in section, of the stapling head during stapling.

Referring to FIG. 5, upon actuation of arms 32 and 34 (FIG. 1) pusher 60 is driven distally within staple head 16 causing pusher fingers 66 and 68 to drive staples 70 out of staple pockets 28. Distal movement of pusher 60 moves knife blade 30 and mainspring 42 distally within staple head 16. Base 44 of knife blade 30 remains engaged with longitudinal rib 74 on shaft 24 thereby preventing rotation of knife blade 30 against the bias of mainspring 42.

Figure 6:
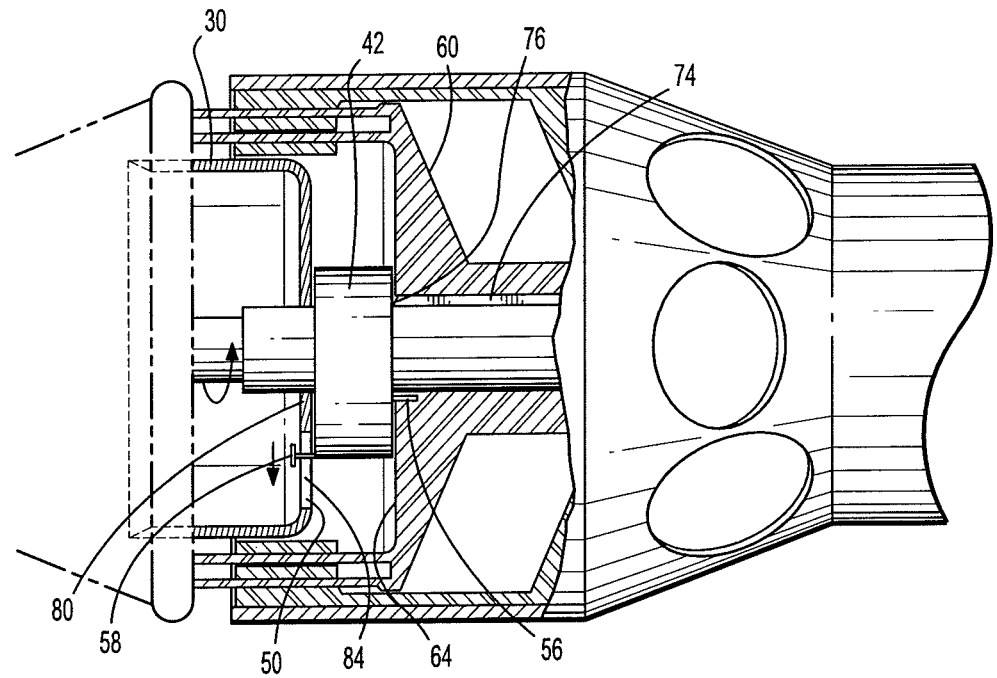
FIG. 6 is a side view, partially shown in section, of the stapling head during actuation of the rotary cutting system.

Referring now to FIG. 6, when knife blade 30 has moved sufficiently a longitudinal distance such that notch 80 in knife blade 30 clears distal end 76 of longitudinal rib 74, the latch mechanism is effectively released and knife blade 30 is free to rotate against the bias of mainspring 42. As mainspring 42 expands from the wound condition to the expanded condition, tab 58 engages, and asserts a force against, edge 84 of slot 50 (see also FIG. 3) thereby causing knife blade 30 to rotate around shaft 24 due to the bias of mainspring 42.

Figure 7:
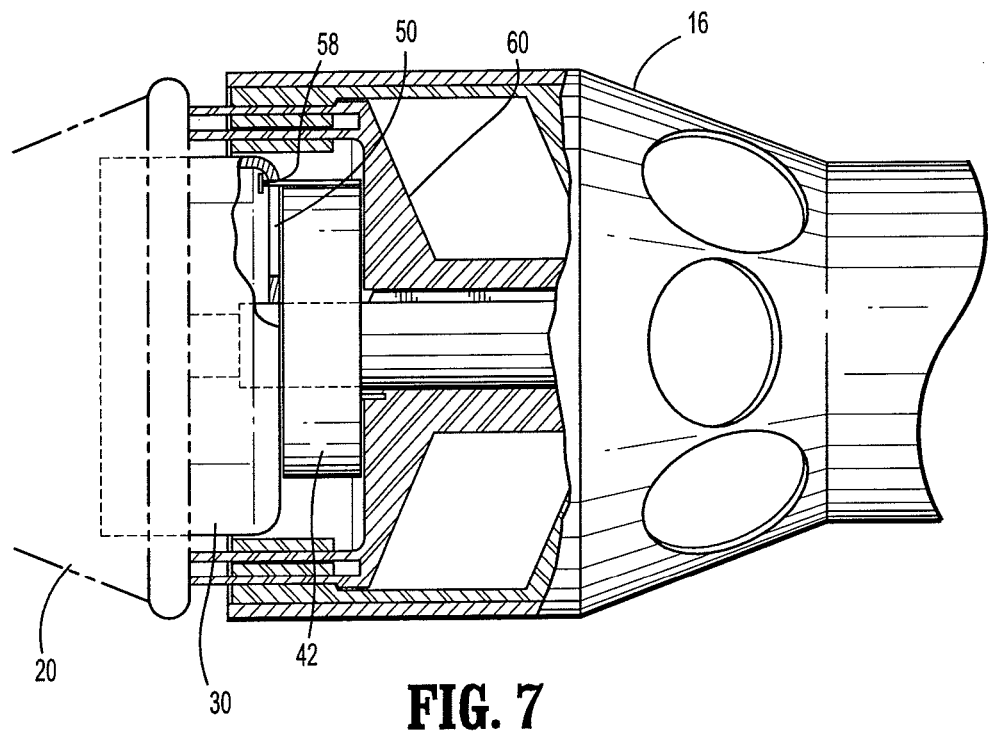
FIG. 7 is a side view, partially shown in section, of the stapling head in the post-fired condition.
Figure 8:
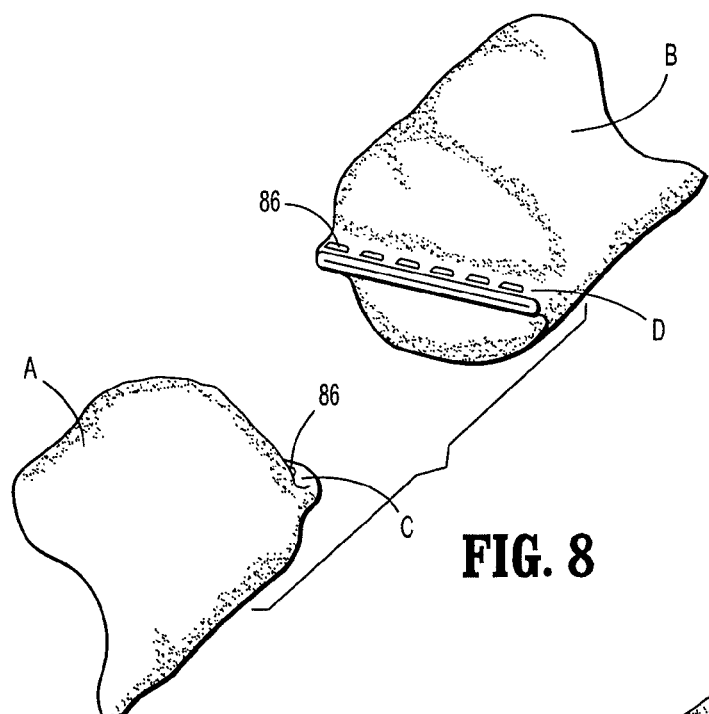
FIG. 8 is a perspective view of cut and stapled free ends of a tubular tissue section.

As best shown in FIG. 7, upon full expansion of mainspring 42, tab 58 moves to a radially outwardly most position within slot 50 in knife blade 30. Thus, the provision of slot 50 allows mainspring 42 to unwind from the wound condition storing energy to the expanded condition releasing energy to knife blade 30 thereby causing knife blade 30 to rotate relative to anvil member 20.

Referring now to FIGS. 8-13, the use of surgical stapling device 10, and specifically, rotary cutting system 40, in tissue will now be described. Initially, a tubular tissue section is operated on in known manner to remove a diseased section of tissue leaving two free healthy tissue sections A and B. During the procedure, the free ends of tissue sections A and B are stapled closed with staples 86 resulting in duckbilled edges C and D. At this point, it is necessary to reconnect tissue sections A and B.

Figure 9:
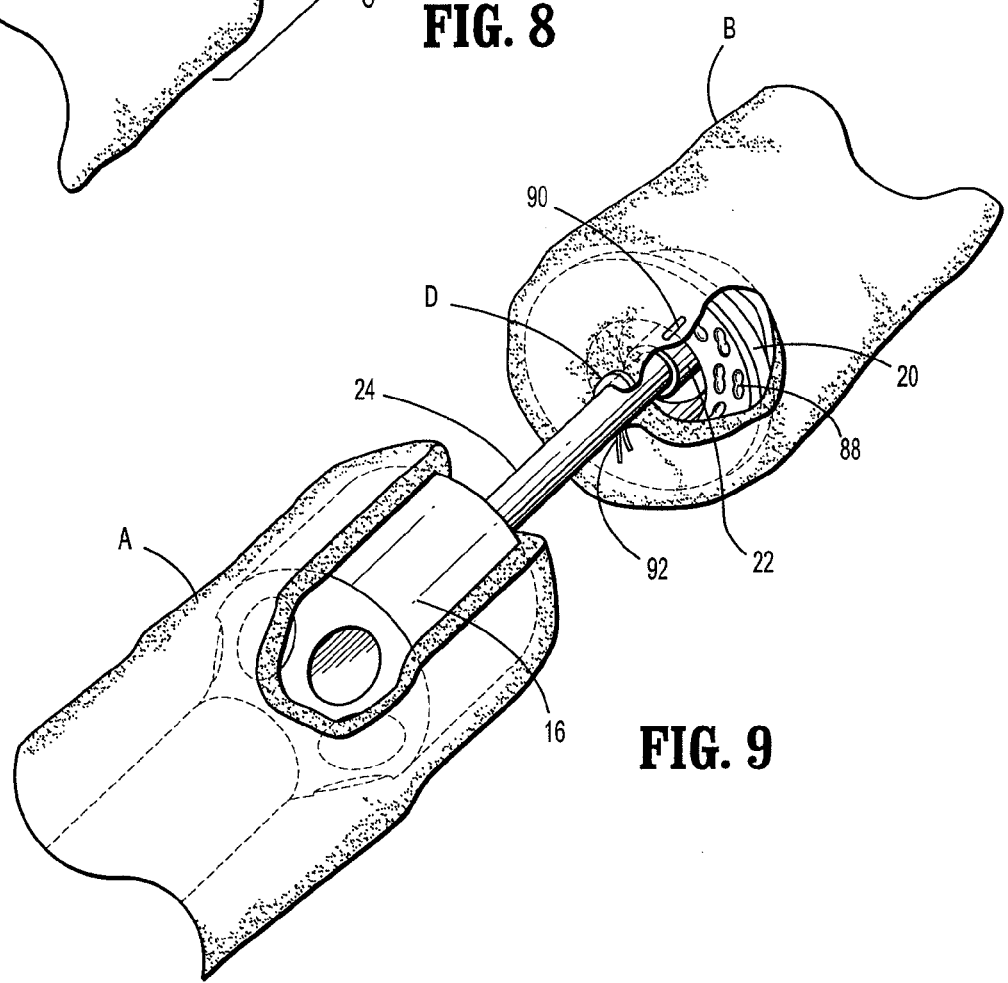
FIG. 9 is a perspective view, partially shown in section, of the free ends of the tubular tissue sections purse stringed about the distal ends of the surgical stapling device inserted therein.

Referring now to FIG. 9, surgical stapling device 10 is advanced through tissue section A to positioned staple head 16. Shaft 24 extends from staple head 16. Anvil member 20 is positioned within tissue section B and a shaft 24 is advanced through duckbilled edges C and D to connect shaft 24 with shaft 22 of anvil member 20. As noted hereinabove, anvil member 20 includes a plurality of staple clinching pockets 88 configured to receive and clench staples 70. As shown, duckbilled edge D is secured about shaft 24 by a purse string suture 92. Likewise, while not specifically shown, duckbilled edge C is also secured about shaft 24 with a purse string suture.

It should be noted that, when cinching tissue sections A and B about shaft 24, bunching of tissue may occur resulting in a wayward staple 90 being positioned within the path of knife blade 30 (not shown). Thus, it is often necessary for knife blade 30 to cut through wayward staple 90 in order to avoid any residual connection between the tissue sections cored out and the resulting joined tissue sections A and B.

Figure 10:
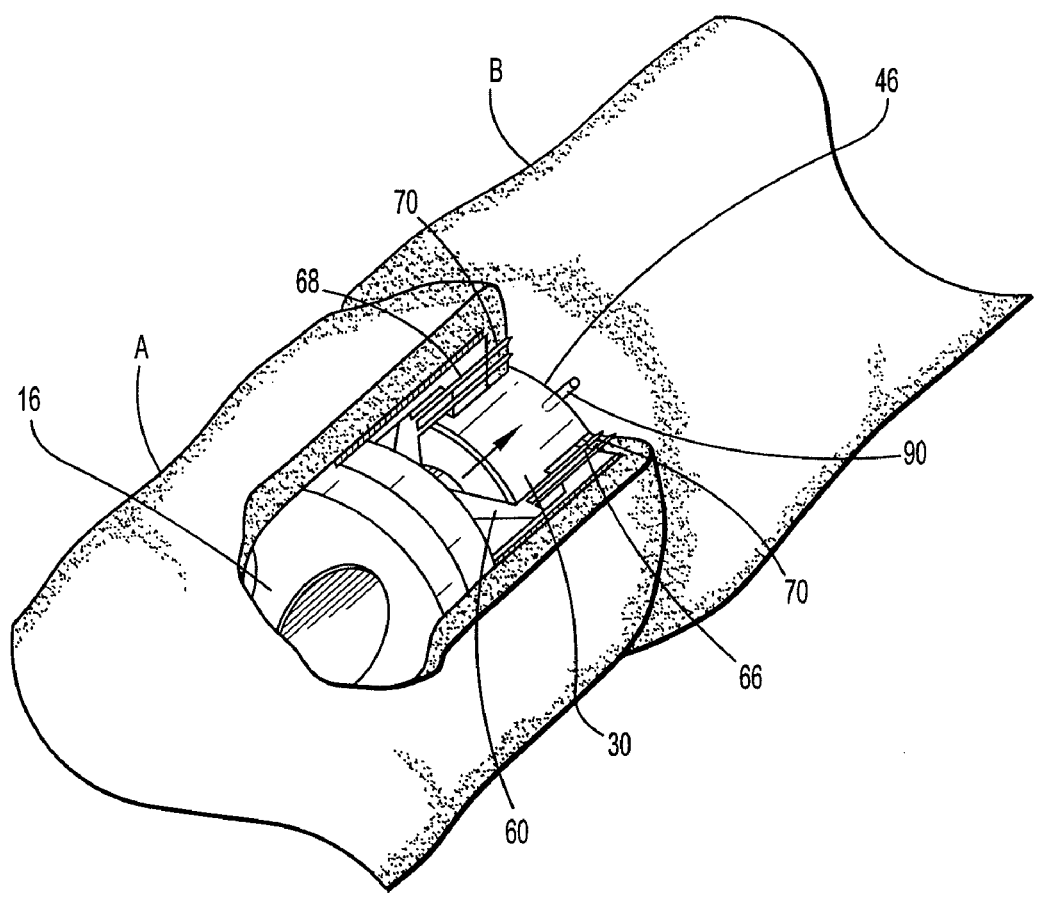
FIG. 10 is a perspective view, partially shown in section, of the tubular tissue sections with an anvil of the surgical stapling device approximated to the stapling head.

Referring now to FIGS. 1 and 10, surgical stapling device 10 is operated by rotating tail member 26 (FIG. 1) to cause anvil member 20 to be approximated adjacent staple head 16 thereby bringing tissue sections A and B together to be stapled. Thereafter, arms 32 and 34 are operated to drive pusher 60 distally thereby causing fingers 66 and 68 to drive staples 70 through tissue sections A and B and into staple clinching pockets 88 of anvil member 20 (FIG. 9). As shown, as knife blade 30 is driven distally, cutting edge 46 of knife blade 30 engages wayward staple 90.

Referring now to FIG. 11, further distal advancement of knife blade 30 causes the disclosed latch mechanism to release knife blade 30 in order to be free to rotate against the bias of mainspring 42 as described hereinabove with regard to FIGS. 4-7. Thus, as knife blade 30 rotates against the bias of mainspring 42, the slicing action of knife blade 30 against wayward staple 90 enhances the ability of knife blade 30 to sever staple 90. Knife blade 30, and specifically cutting edge 46 of knife blade 30, engages a knife ring 94 formed within anvil member 20 which serves as an abutment surface for cutting edge 46.

With specific reference to FIG. 12, it can be seen that rotating knife blade 30 severs wayward staple 90 into first and second wayward portions 96 and 98. Pusher fingers 68 drive staples 70 into staple clinching pockets 88 of anvil member 20 to thereby staple the tissue sections together. Once the tissue sections have been severed by knife blade 30, the cored out tissue section CS remains with severed half 98 of wayward staple 90 attached thereto. In this manner, rotary cutting system 40 ensures that there is no connection remaining between cored tissue section CS and the remaining now stapled tissue sections A and B.

As best shown in FIG. 13, tissue sections A and B are stapled together by circular ring of staples 70 passing through inward edge IEA of tissue section A and inward edge IEB of tissue section B. First half 96 of wayward staple 90 remains with the tissue sections and deteriorates or detaches and thus passes out of the body over time.

Figures 14, 15, 16, 17:
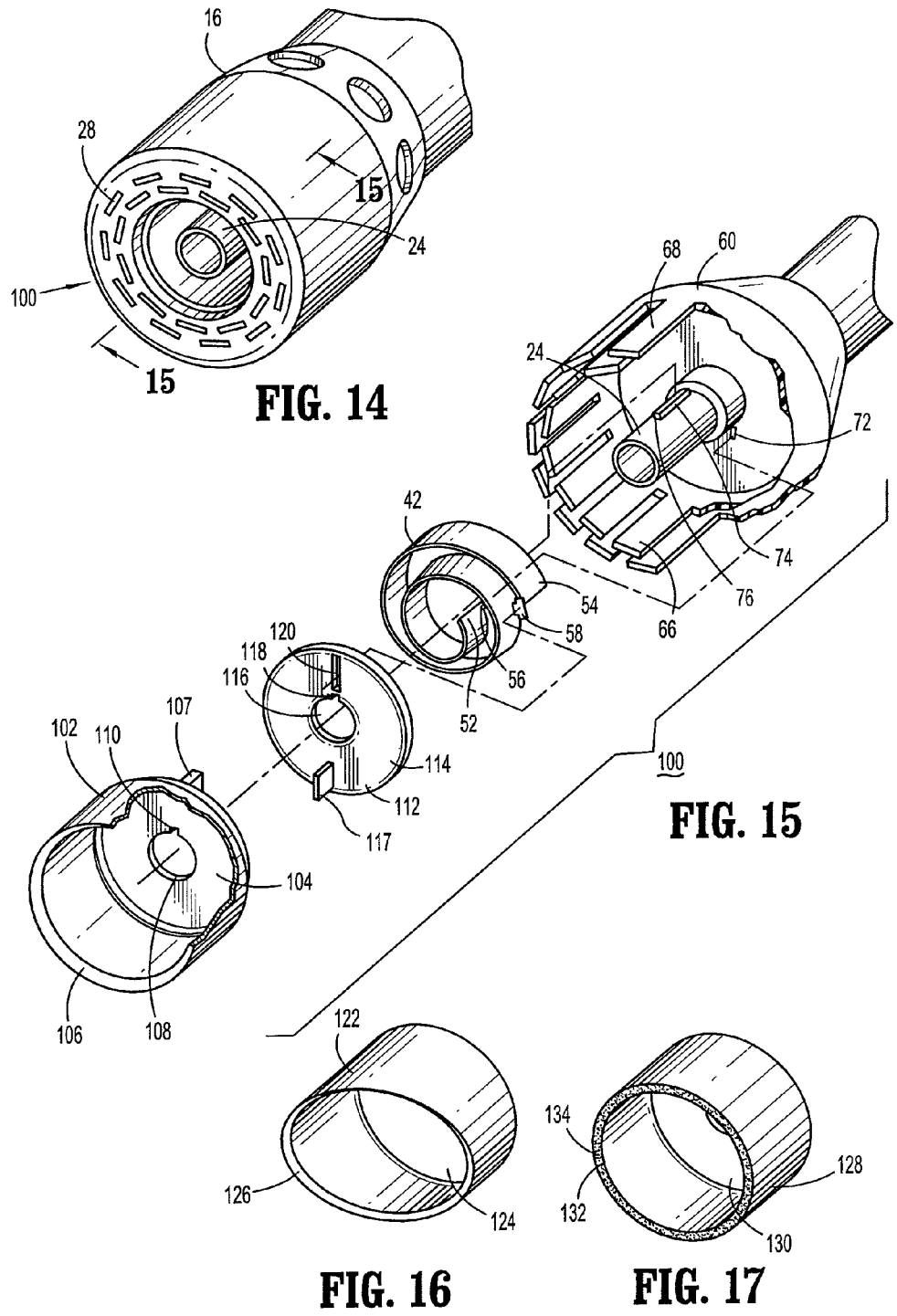
FIG. 14 is an enlarged perspective view of the stapling of the surgical stapling device of FIG. 1 incorporating an alternative embodiment of a rotary cutting system.
FIG. 15 is a perspective view, with parts separated, of the stapling head of FIG. 14.
FIG. 16 is a perspective view of a first alternative cutting blade for use in the disclosed rotary cutting systems.
FIG. 17 is a perspective view of a second alternative cutting blade for use in the disclosed rotary cutting systems.

Referring now to FIGS. 14 and 15, and initially with regard to FIG. 14 there is disclosed an alternative rotary cutting system 100 for use with surgical stapling device 10. As best shown in FIG. 15, rotary cutting system 100 generally includes pusher 60 and mainspring 42 substantially as described hereinabove. Additionally, rotary cutting system 100 includes a circular knife blade 102 having a proximal base 104 and a distal cutting edge 106. Knife blade 102 further includes a central opening 108 configured to receive and move along shaft 24 of surgical stapling device 10. A notch 110 is formed in opening 108 to accommodate rib 74 on shaft 24.

Rotary cutting system 100 additionally includes a rotatable hammer 112 having a first surface 114 for fractional engagement with proximal base 104 of knife blade 102. Unlike rotary cutting system 40 described hereinabove, in rotary cutting system 100, hammer member 112 is connected to mainspring 42 and rotated thereby. Fractional engagement of hammer member 112 with knife blade 102 rotates knife blade 102 to slice through tissue. Hammer member 112 also includes a central opening 116 for receipt of shaft 24 and a notch 118 for receipt of longitudinal rib 74. Hammer member 112 also includes a slot 124 engagement with mainspring 42. While not specifically shown, staples 70, identical to those described hereinabove, are engageable with circular arrays of pusher fingers 66 and 66 as described above.

Referring for the moment to FIG. 16., there is disclosed in alternative knife blade 122 having a proximal base 124 and a distal cutting edge 126. In this embodiment, distal cutting edge 126 of knife blade 122 is oriented at an angle relative to proximal base 124. Upon rotation, this angular orientation of distal cutting edge 126 facilitates slicing through wayward staples or tough tissues.

Referring to FIG. 17, there is disclosed a further alternative embodiment of a knife blade 128 having a proximal base 130 and a distal cutting edge 132. In this embodiment, distal cutting edge 132 may be formed with a serrated surface 134. Alternatively, surface 134 may be coated with abrasive or other materials to facilitate cutting through wayward staples and tough tissues.

Figure 18:
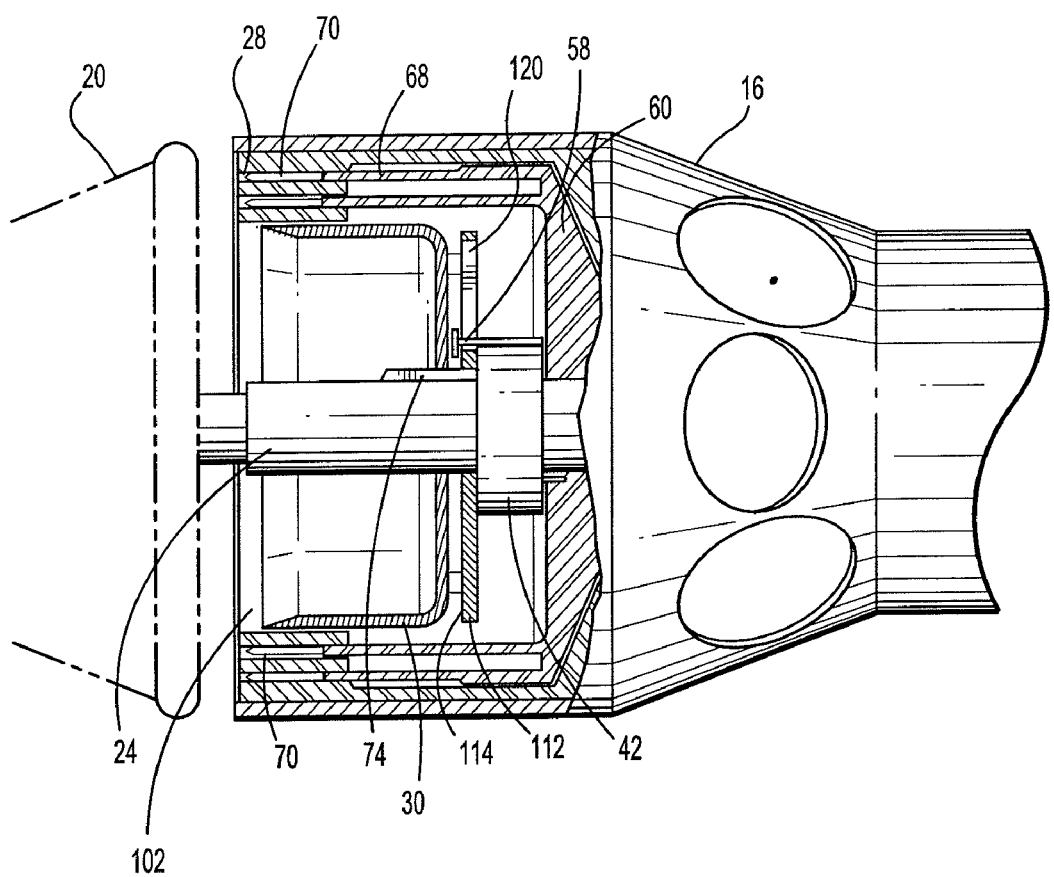
FIG. 18 is a side view, partially shown in section, of an anvil and the stapling head of FIG. 14 in a pre-fired condition.
Figure 19:
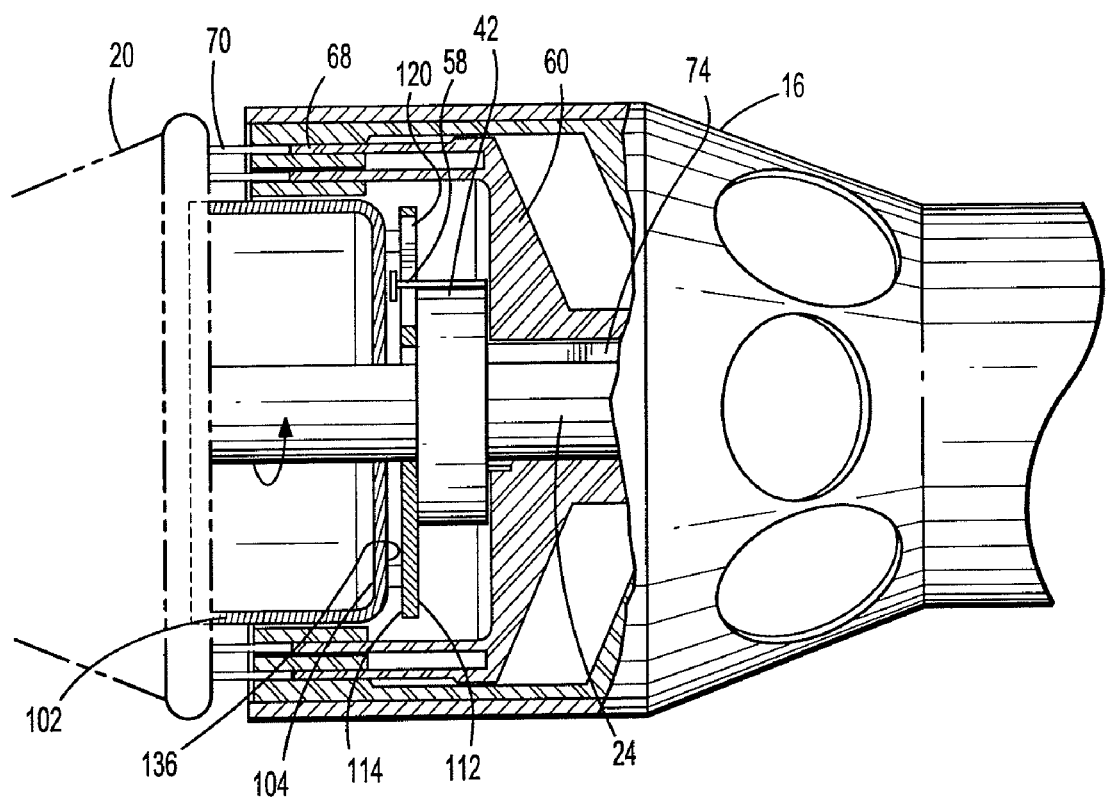
FIG. 19 is a side view, similar to FIG. 18, during actuation of the rotary cutting system.
Figure 20:
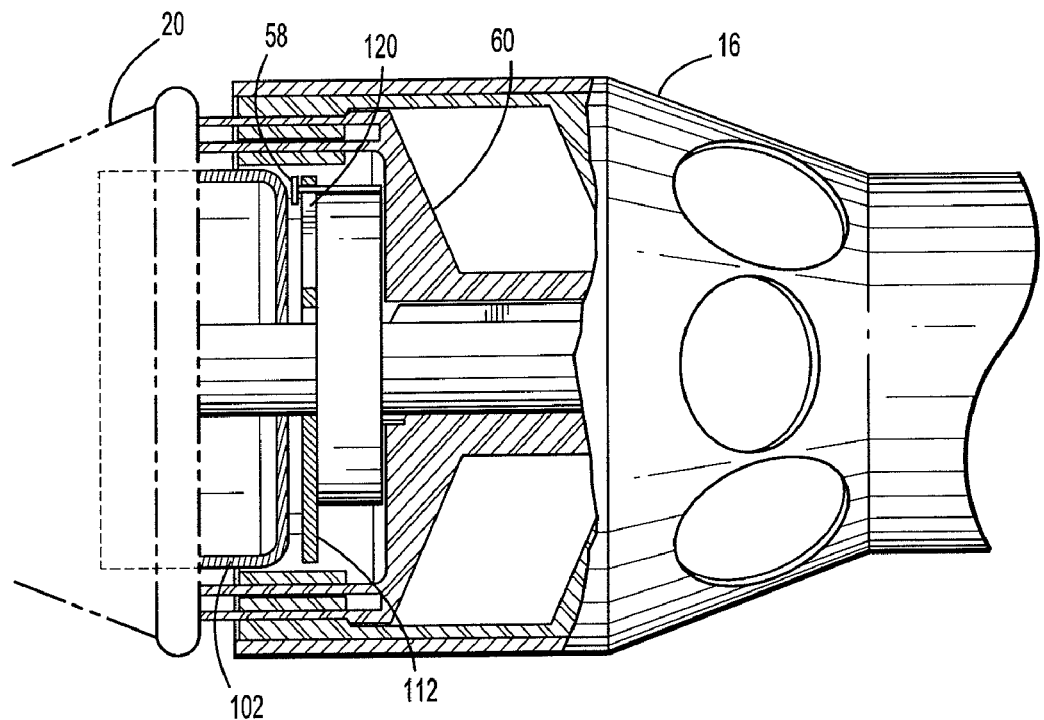
FIG. 20 is a side view, similar to FIG. 19, after actuation of the rotary cutting system.

Referring now to FIGS. 18-20, the operation of rotary cutting system 100 will now be described. Referring initially to FIG. 18, pusher 60 is in a proximal most position within staple head 16 and mainspring 42 is in the fully wound condition with tab 58 of mainspring 42 positioned within slot 120 in hammer member 112. Staples 70 are positioned within staple pockets 28 ahead of pusher fingers, for example pusher fingers 68. Knife blade 102 and hammer member 112 are restrained against rotation by longitudinal ribs 74.

Referring to FIG. 19, upon actuation of surgical stapling device 10 (FIG. 1) pusher 60 is driven distally over shaft 24 and the latch mechanism is released allowing hammer member 112 to rotate against the bias of spring mainspring 42. Specifically, as hammer member 112 clears the longitudinal rib 74 it is free to rotate due to the bias of mainspring 42. Tab 58 of mainspring 42 moves radially outwardly within slot 120 in hammer member 112 causing hammer member 112 to rotate. Rotation of hammer member 112 forces first surface 114 into fractional engagement with a undersurface 136 of proximal base 104 of knife blade 102. Fractional engagement of undersurface 136 with hammer first surface 114 causes knife blade 102 to rotate to thereby slice through wayward staples and any tough tissues. As shown, distal movement of pusher 60 causes pusher fingers 68 to drive staple 70 into anvil member 20.

Referring now to FIG. 20, upon full rotation of hammer member 112, tab 58 of mainspring 42 moves completely radially outwardly within slot 120 of hammer member 112. Thus, in this manner, fractional engagement of hammer member 112 with knife blade 102 allows hammer member 112 to impart substantial momentum and rotational movement to knife blade 102. Depending upon the degree of frictional engagement between hammer member 112 and 102, a predetermined amount of slip may occur between hammer member 112 and knife blade 102 in the event knife blade 102 gets stuck. This prevents knife blade 102 from tearing tissue due to continued rotation in the presence of a stuck condition.

It will be understood that various modifications may be made to the embodiments disclosed herein. For example, other means of storing rotational energy may be provided such as, for example, torsion or other springs capable of storing rotational energy. Furthermore, rotational energy to a knife blade may be provided by forming a distal end of the longitudinally extending rib in a helical manner allowing the knife blade to move distally and rotate with the helically extending longitudinal rib. Additionally, other treatments may be provided to the cutting edge of the knife blade to facilitate cutting through metallic staples or other prosthetic material in the path of the knife blade. Therefore, the above description should not be construed as limiting, but merely as exemplifications of particular embodiments. Those skilled in the art will envision other modifications within the scope and spirit of the claims appended hereto.

The invention claimed is:

1. A rotary cutting system for use with a surgical stapling device comprising:
   a knife blade having a distal cutting edge and a proximal base;
   a support base positioned within a surgical stapling device;
   a mainspring for imparting a motion to the knife blade relative to the support base; and
   a releasable latch mechanism engagable with the knife blade to releasably restrain the knife blade against the bias of the mainspring, wherein a first end of the mainspring is attached to the support base and a second end of the mainspring is engageable with the knife blade, and the mainspring is a length of material spiral coiled upon itself and expandable from a wound condition storing energy to an expanded condition releasing energy such that the mainspring imparts rotary motion to the knife blade relative to the support base as the mainspring moves from the wound condition to the expanded condition.

2. The rotary cutting system as recited in claim 1, wherein the knife blade is a circular cutting blade and the second end of the mainspring is engagable with the proximal base of the knife blade.

3. The rotary cutting system as recited in claim 2, wherein the distal cutting edge of the knife blade is angled relative to the proximal base of the knife blade.

4. The rotary cutting system as recited in claim 2, wherein the distal cutting edge of the knife blade is serrated.

5. The rotary cutting system as recited in claim 2, wherein the proximal base of the knife blade has a slot and the second end of the mainspring has a tab engagable within the slot such that the tab moves radially outward within the slot as the mainspring moves from the wound condition to the expanded condition.

6. The rotary cutting system as recited in claim 2, wherein the support base is a staple pusher positioned within a staple head of the surgical stapling device.

7. The rotary cutting system as recited in claim 6, wherein the knife blade, mainspring and staple pusher are movably mounted on a longitudinal shaft inside the staple head such that the knife blade is longitudinally movable along the shaft.

8. The rotary cutting system as recited in claim 7, wherein the latch mechanism includes a protrusion formed on the shaft and a notch formed in the knife blade and engagable with the protrusion such that the knife blade is restrained against rotary motion when the notch is engaged with the protrusion and is free to rotate due to the bias of the mainspring when the notch is disengaged from the protrusion.

9. A rotary cutting system for use with a surgical stapling device comprising:
  a knife blade having a distal cutting edge and a proximal base;
  a support base positioned within a surgical stapling device;
  a mainspring for imparting motion to the knife blade relative to the support base; and
  a releasable latch mechanism engagable with the knife blade to releasably restrain the knife blade against the bias of the mainspring, wherein a first end of the mainspring is attached to the support base and a second end of the mainspring is engageable with the knife blade, the first end of the mainspring located radially inward of the second end of the mainspring.

10. The rotary cutting system as recited in claim 9, wherein the mainspring is a length of spring steel.

* * * * *